(12) United States Patent
Witt et al.

(10) Patent No.: US 7,670,480 B2
(45) Date of Patent: Mar. 2, 2010

(54) SOLVENT SUPPLY WITH CORRECTION OF PISTON MOVEMENT

(75) Inventors: Klaus Witt, Keltern (DE); Konstantin Choikhet, Karlsruhe (DE); Alexander Bierbaum, Karlsruhe (DE)

(73) Assignee: Agilent Technologies, Inc., Santa Clara, CA (US)

( * ) Notice: Subject to any disclaimer, the term of this patent is extended or adjusted under 35 U.S.C. 154(b) by 965 days.

(21) Appl. No.: 11/386,978

(22) Filed: Mar. 22, 2006

(65) Prior Publication Data

US 2006/0219618 A1    Oct. 5, 2006

Related U.S. Application Data

(60) Provisional application No. 60/667,165, filed on Mar. 31, 2005.

(30) Foreign Application Priority Data

Mar. 31, 2005    (EP)    .................................. 05102533

(51) Int. Cl.
*B01D 17/12*    (2006.01)
*F04B 49/00*    (2006.01)
*B01D 15/08*    (2006.01)

(52) U.S. Cl. .......................... 210/101; 73/61.56; 137/7; 137/87.01; 210/103; 210/143; 210/198.2; 210/656; 210/739; 210/741; 417/4; 417/5; 417/44.2; 417/53; 366/152.1; 366/348

(58) Field of Classification Search ................ 73/61.52, 73/61.56; 210/101, 103, 143, 198.2, 656, 210/739, 741; 204/600–602; 417/2–6, 18, 417/20, 36, 38, 43, 44.2, 53, 216, 286, 415, 417/426, 504, 540; 700/273, 275, 281, 282; 137/7, 87.01; 366/152.1, 348

See application file for complete search history.

(56) References Cited

U.S. PATENT DOCUMENTS 4,032,445 A * 6/1977 Munk .......................... 210/103

(Continued)

FOREIGN PATENT DOCUMENTS

EP    0 309 596    9/1987

(Continued)

OTHER PUBLICATIONS

Zhou, X., et al., New Micro-Flow Pumping System For Liquid Chromatography, Journal of Chromatography A, 2001, pp. 165-171.

(Continued)

*Primary Examiner*—Joseph W Drodge
(74) *Attorney, Agent, or Firm*—Marc Bobys

(57) ABSTRACT

A supply flow path for supplying a solvent is described. The supply flow path includes metering devices each with a piston, the metering devices being adapted for metering the solvent through separate source paths feeding the supply flow path. The supply flow path further includes a control unit adapted for controlling the metering devices' piston movement in accordance with solvent pressure, wherein a variation of the solvent pressure gives rise to a corresponding variation of a solvent volume contained in the supply flow path or a part thereof. The control unit is adapted for compensating for the variation of the solvent volume by corresponding movements or forward or backward displacements of the pistons.

11 Claims, 8 Drawing Sheets

U.S. PATENT DOCUMENTS

| | | | | |
|---|---|---|---|---|
| 4,043,906 A | * | 8/1977 | Helmer | 210/659 |
| 4,225,290 A | | 9/1980 | Allington | |
| 5,450,743 A | | 9/1995 | Buote | |
| 5,630,706 A | * | 5/1997 | Yang | 417/3 |
| 2003/0052007 A1 | | 3/2003 | Paul et al. | |

FOREIGN PATENT DOCUMENTS

WO  WO 03/079000 A1  9/2003

OTHER PUBLICATIONS

European Search Report dated Sep. 12, 2005.

* cited by examiner

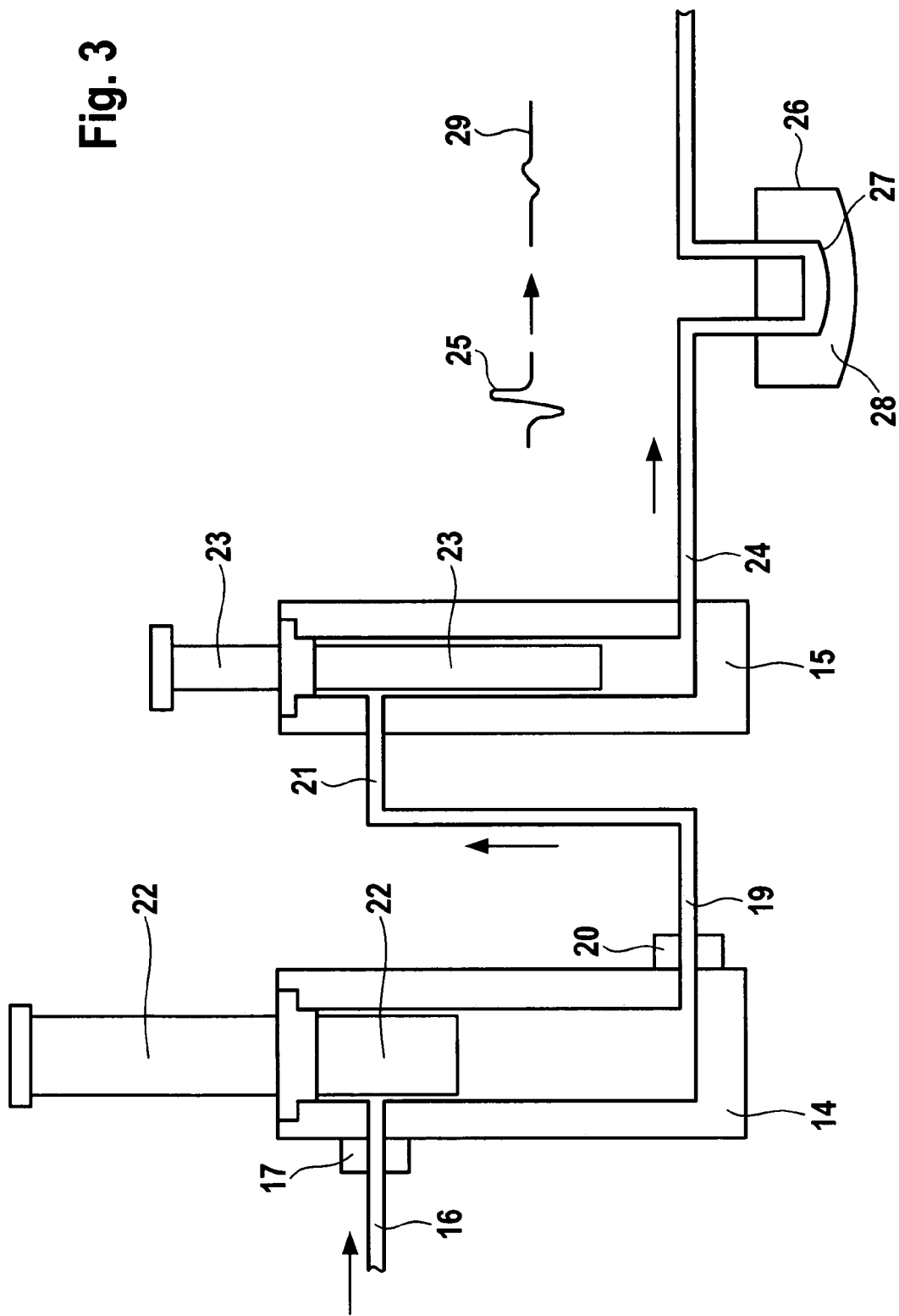

Fig. 10A
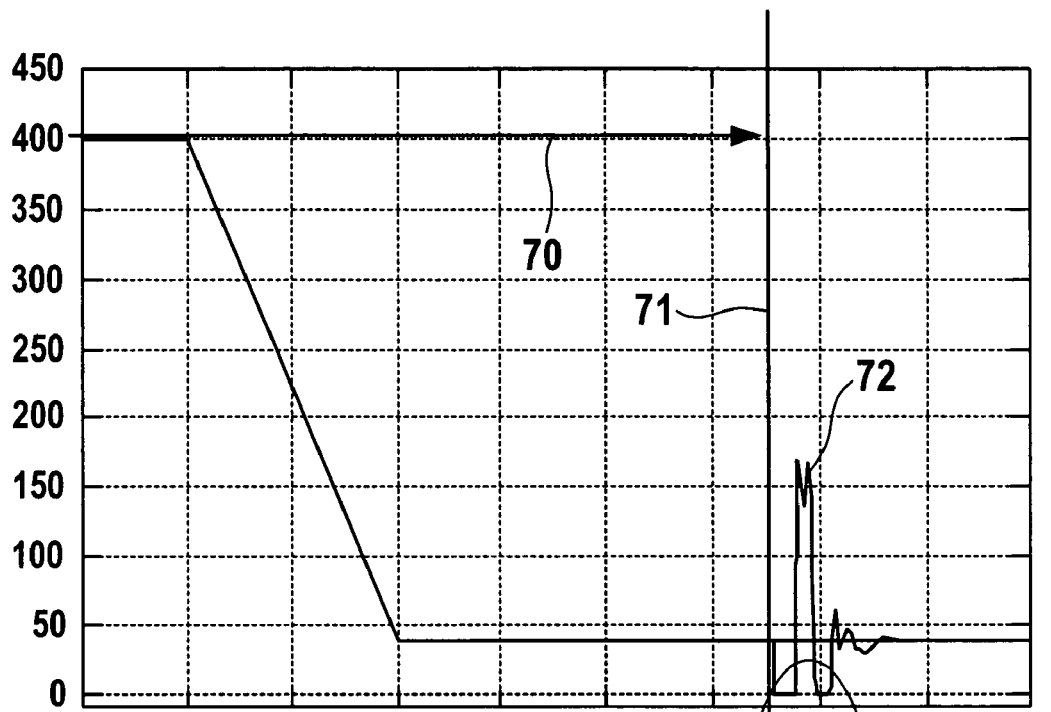
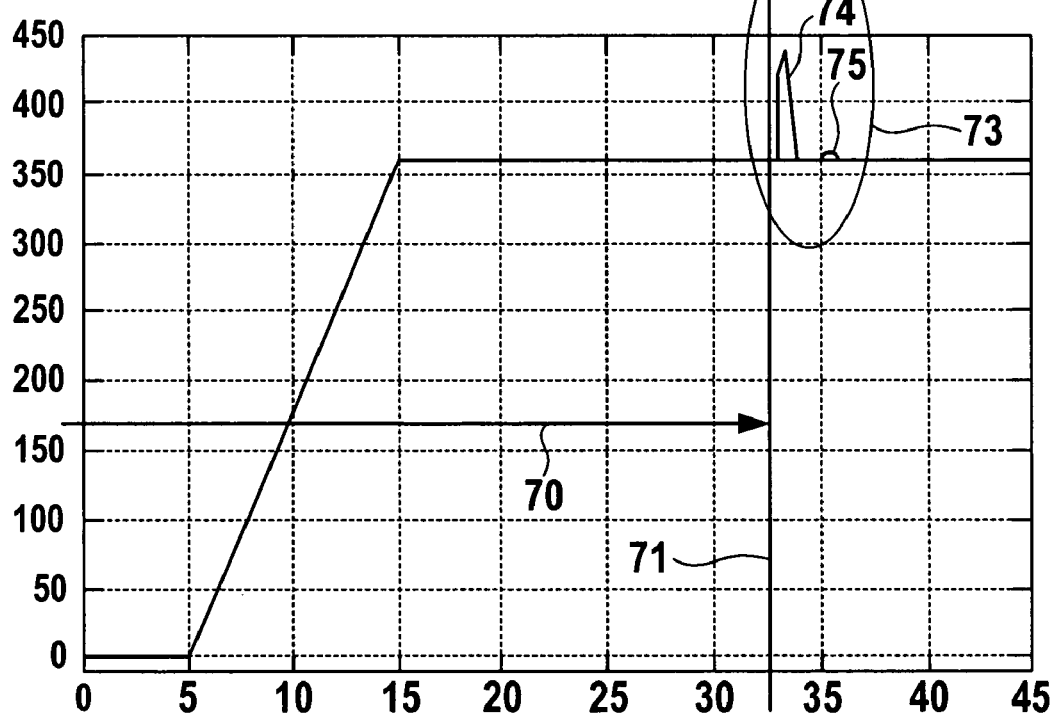
Fig. 10B

SOLVENT SUPPLY WITH CORRECTION OF PISTON MOVEMENT

CROSS-REFERENCE TO RELATED APPLICATIONS

This application claims priority from U.S. Provisional Patent Application No. 60/667,165, filed on Mar. 31, 2005.

BACKGROUND ART

The present invention relates to a supply flow path for supplying a solvent, to a solvent supply system, and to a separation system adapted for separating compounds of a fluid sample. The invention further relates to a method for supplying a solvent, and to a method for generating a composite solvent with a time-dependent solvent composition.

Solvent delivery systems are used to source single-component liquids or mixtures of liquids at pressures which can range from substantially atmospheric pressure to pressures on the order of several hundred bar.

In U.S. patent application Publication No. US 2004/0108273 A1 "Backflow Prevention for High Pressure Gradient Systems", a high pressure gradient solvent delivery system is described. The compositional accuracy of high pressure gradient pumps is improved by adding pulse dampening with backflow prevention to each high pressure pump. The backflow prevention adds sufficient minimum flow resistance whereby enhancing the performance of the pulse dampening over a wider range of flow rates resulting in consistent gradient performance.

DISCLOSURE

It is an object of the invention to improve the precision of a solvent supply system. The object is solved by the independent claim(s). Preferred embodiments are shown by the dependent claim(s).

According to embodiments of the present invention, a supply flow path for supplying a solvent comprises a metering device with a piston, whereby the metering device is adapted for metering the solvent. The supply flow path further comprises a control unit adapted for controlling the metering device's piston movement in accordance with solvent pressure, wherein a variation of the solvent pressure gives a rise to a corresponding variation of a solvent volume contained in the supply flow path or a part thereof. The control unit is adapted for compensating for the variation of the solvent volume by a corresponding corrective movement of the piston.

Pressure variations at the outlet of the supply flow path affect the solvent volume stored in the supply flow path. For example, if the solvent pressure rises, the solvent volume in the supply flow path will be compressed. If there is a pressure drop, an expansion of the solvent volume in the supply flow path will be observed. Because of these volumetric changes introduced by pressure variations, there is no one-to-one correspondence between the solvent volume displaced by the piston and the flow rate of solvent at the outlet of the supply flow path. In fact, the flow rate at the outlet does not only depend on the piston movement, but also depends on the instantaneous solvent pressure. The absolute value of volumetric changes introduced by pressure variations is dependent on the total volume of liquid in the supply flow path and its elasticity, so the relative disturbance on the flow rate at the outlet rises when the flow rate is low. Additionally systematic pressure slopes might e.g. arise from steep gradients that are used especially in high throughput applications.

According to embodiments of the present invention, the control unit is adapted for controlling the piston movement in a way that effects due to pressure variations are taken into account. First, the piston's velocity is set to a desired flow rate and the solvent pressure is monitored. In case of pressure variations, a corrective movement that corresponds to the pressure-induced variation of the solvent volume in the supply flow path is superposed on the regular piston movement. Thus, the expansion or compression of the solvent volume contained in the supply flow path is compensated for. As a result, a solvent flow having the desired flow rate is obtained at the outlet of the supply flow path.

In a lot of applications, it is not possible to keep system pressure at a constant value. But even if system pressure is subjected to pressure variations, the supply flow path according to embodiments of the present invention will deliver a highly accurate solvent flow.

According to a preferred embodiment, the supply flow path comprises a pressure determination unit adapted for tracking solvent pressure in the supply flow path. For example, the pressure determination unit might generate a signal indicating the actual pressure, and said signal might be forwarded to the metering device's control unit, in order to adapt the piston movement to the pressure variation.

In a preferred embodiment, the control unit is adapted for superposing a correction on the piston movement, in order to stabilize the flow rate at the outlet of the supply flow path. Thus, distortions and discontinuities of the flow rate are removed. For example, in the field of sample analysis, a stabile flow rate helps to improve the accuracy of the acquired measurement data.

In a preferred embodiment, the control unit is adapted for compensating for an additional compression or expansion flow due to the variation of the solvent pressure by modifying the metering device's piston movement, whereby an additional solvent quantity pushed into or drawn out of the supply flow path is compensated for. Such compression or expansion flow might e.g. include the effects of solvent compressibility and system elasticity. System elasticity might e.g. include damping elements.

According to a preferred embodiment, the control unit is adapted for compensating for an increase of the solvent pressure by superposing a corresponding forward displacement on the piston movement. The control unit is further adapted for compensating for a decrease of the solvent pressure by superposing a corresponding backward displacement on the piston movement. A forward displacement of the piston corresponds to a volume compression of the solvent in the supply flow path. Correspondingly, a backward displacement of the piston corresponds to a volume expansion of the solvent in the supply flow path.

Embodiments of the present invention further relate to a solvent supply system comprising a first supply flow path as described above, with the first supply flow path being adapted for supplying a first solvent to a mixing unit. The solvent supply system further comprises a second supply flow path comprising a second metering device with a piston, the second supply flow path being adapted for supplying a second solvent to the mixing unit. The mixing unit is adapted for mixing the first and the second solvent and for supplying a composite solvent with a mixing ratio of the first and the second solvent. The control unit is adapted for such controlling the piston movements of the first and the second metering device that the mixing ratio becomes substantially independent of a variation of the solvent pressure of the composite solvent.

In prior art solutions, a variation of solvent pressure at the mixing unit's outlet affected the flow rates provided by the first and the second supply flow path. For example, in case of a pressure increase, both the first solvent stored in the first supply flow path and the second solvent stored in the second supply flow path have been subjected to further compression. As a result, the pressure change affected the effective flow rates provided by the first and the second supply flow path.

Furthermore, variations of the composite solvent's pressure may affect the mixing ratio of the first and the second solvent. The flow rate provided by the first supply flow path might differ significantly from the flow rate provided by the second supply flow path. Furthermore, the compressibility in the first supply flow path might differ from the compressibility in the second supply flow path. For these reasons, the volumetric effects caused by the pressure variations might affect the respective flow rates to a different extent, and hence, a pressure variation may affect the solvents' mixing ratio.

In prior art solvent supply systems, the above-described pressure dependence of the composite solvent's mixing ratio had a negative effect on the precision of acquired data. Furthermore, for certain parameter ranges, oscillations of system pressure have been encountered. The reason for these oscillations is that system pressure affects the solvents' mixing ratio, and in turn, the mixing ratio affects system pressure through viscosity changes of such mixed liquids.

In the solvent supply system according to embodiments of the present invention, the volumetric effects due to pressure variations are compensated for. Because of these volumetric effects, there is no one-to-one correspondence between the piston's velocity and the flow rate obtained at a supply flow path's outlet. Accordingly, in embodiments of this invention, the piston movement is such modified that both the desired flow rate and the effects due to pressure variations are taken into account. Any additional compression or expansion of the solvent contained in the supply flow path is compensated for. By utilizing a pressure-corrected piston movement, the mixing ratio becomes substantially independent of any variations of the composite solvent's pressure. The percentage of the first and the second solvent is no longer affected by pressure variations, and hence, a composite solvent having a highly precise solvent composition is provided at the mixing unit's outlet. By stabilizing the composite solvent's mixing ratio, the accuracy of subsequent measurements is improved.

According to a preferred embodiment, the control unit is adapted for compensating for an additional compression or expansion flow due to the variation of the solvent pressure. This can be accomplished by such modifying the metering devices' piston movements, in each of the first and the second supply flow path, that solvent quantities pushed into or drawn out of the respective supply flow path are compensated for.

In a preferred embodiment, the control unit is adapted for counteracting an expansion or compression of the solvent volumes in the supply flow paths, which is due to a variation of the solvent pressure, by compensatory movements superposed on the piston movements.

According to another preferred embodiment, the control unit is adapted for compensating for an increase of the solvent pressure by superposing corresponding forward displacements on the piston movements. Further preferably, the control unit is adapted for compensating for a decrease of the solvent pressure by superposing corresponding backward displacements on the piston movements.

In a preferred embodiment, forward displacements of the pistons correspond to volume compressions of the first and the second solvent in the first and the second supply flow path, and backward displacements of the pistons correspond to volume expansions of the first and the second solvent in the first and the second supply flow path.

According to an alternatively preferred embodiment, the control unit is adapted for dampening or suppressing oscillations of the composite solvent's mixing ratio, which are caused by pressure variations, by superposing a compensatory stimulus pulse on at least one of the piston movements of the first and the second metering device.

In solvent supply systems of the prior art, a change of the composite solvent's pressure affects both the volume of solvent A contained in the first supply flow path and the volume of solvent B in the second supply flow path. In dependence on the flow rates and on the compressibilities in the two supply flow paths, the mixing ratio of solvent A and solvent B might be modified. In turn, the modified mixing ratio might affect the composite solvent's viscosity and thus the pressure. Thus, the interplay between mixing ratio and solvent pressure gives rise to oscillations of the mixing ratio and to corresponding oscillations of solvent pressure.

According to embodiments of the present invention, this oscillatory behaviour is counteracted by superposing corrective displacements on the piston movements. In the embodiments that have been described so far, these corrections are steadily applied right from the beginning. However, for suppressing the undesired oscillatory behaviour, it might be sufficient to superpose a short correction pulse on at least one of the first and the second metering device's piston movement. In response to this stimulus pulse, the oscillations are suppressed almost immediately. In this embodiment, the overhead required for performing the correction is kept as small as possible.

According to a preferred embodiment, the mixing unit is implemented as a mixing tee. In the mixing tee, the flow of solvent A is merged with the flow of solvent B, with the mixture of solvent A and solvent B being provided at the mixing tee's outlet.

According to another preferred embodiment, the solvent supply system further comprises a pressure determination unit adapted for determining the pressure of the solvent behind the mixing unit. The composite solvent's pressure may vary in dependence on solvent composition. By monitoring the pressure variation, the required corrective movements for the pistons can be determined.

According to yet another embodiment, the piston movements of the first and the second flow path are such controlled that the composite solvent is supplied at a constant flow rate. For example, in the field of analysing fluid samples, analysis of acquired data is considerably simplified when the composite solvent's flow rate is kept constant.

In a preferred embodiment, the mixing ratio of the first and the second solvent changes as a function of time. Thus, the properties of the composite solvent may vary as a function of time, e.g. in a programmed manner.

In a further preferred embodiment, the control unit is adapted for such controlling the piston movements of the first and the second metering device that the ratio of the first and the second solvent is continuously varied. According to a further preferred embodiment, the ratio of the first and the second solvent is varied according to a gradient. For example, analytical conditions might require the mobile phase composition to change over the course of the analysis. For example, in liquid chromatography, the elution strength of the mobile phase often is programmed to increase continuously as a function of time.

According to another preferred embodiment, the required correction of the piston movement is derived from one or more of the following parameters: actual pressure of the individual solvents or the composite solvent, system elasticity (damping) of the supply flow path components, respective compressibilities in the first and the second supply flow path, actual piston positions of the metering devices. From a metering device's piston position, the solvent volume contained in the respective supply flow path can be determined. As soon as the pressure variation, the system elasticity, the compressibility in a supply flow path and the solvent volume stored in the supply flow path are known, the resulting compression or expansion of the solvent volume can be derived there from. The change of solvent volume determines the required compensatory displacement of the piston.

In a preferred embodiment, respective compressibilities in the first and the second supply flow path are determined before delivering the composite solvent. For example, a compressibility in a supply flow path might be determined by monitoring the solvent pressure while compressing the solvent volume stored in the supply flow path, preferably by the action of displacing the piston.

In a preferred embodiment, the variation of the composite solvent's pressure is due to a corresponding variation of the composite solvent's viscosity. For example, the mixing unit's outlet might be connected to a device having a certain hydraulic resistance. The composite solvent's pressure required for passing composite solvent through the device depends both on the device's hydraulic resistance and on the composite solvent's viscosity. In turn, the composite solvent's viscosity might depend on the mixing ratio of the first and the second solvent. Hence, the mixing ratio affects the viscosity, whereby a variation of the composite solvent's viscosity leads to a corresponding variation of solvent pressure at the mixing unit's outlet.

According to a preferred embodiment, the control unit is adapted for deriving the composite solvent's pressure from a known relation between solvent pressure and solvent composition. For example, solvent pressure might be recorded as a function of the mixing ratio of the first and the second solvent. As soon as the relation between solvent pressure and mixing ratio is known, this relation can be used for forecasting the pressure of the composite solvent at the mixing unit's outlet. In this embodiment, it is no longer necessary to actually measure the composite solvent's pressure.

In a further preferred embodiment, at least one of the first and the second supply flow path comprises a damping unit. A damping unit is adapted for flattening out discontinuities of system pressure. For example, the damping unit might comprise a fluid reservoir that is separated from the supply flow path by means of an elastic membrane.

According to a preferred embodiment, the solvent supply system is part of a microfluidic device.

According to a preferred embodiment, the solvent supply system is in fluid connection with a separation device, with the composite solvent being used as a mobile phase, in order to separate compounds of a fluid sample. For example, the mobile phase might be conveyed through the fluid passageways of a stationary phase support where separation of dissolved analytes can occur. The stationary phase support may e.g. comprise a packed bed of particles, a membrane or collection of membranes, a porous monolithic bed, or an open tube. Often, analytical conditions require the mobile phase composition to change over the course of the analysis, in order to perform a gradient elution. In applications of this kind, measurement accuracy highly depends on the metering precision of the solvent supply system. For example, measurement accuracy might depend on the precision of the first and the second solvent's mixing ratio, because this mixing ratio determines properties such as e.g. the composite solvent's elution strength.

In a preferred embodiment, water is used as a first solvent, whereas an organic solvent such as e.g. ethanol or acetonitrile is used as a second solvent. By continuously increasing the amount of organic solvent, the composite solvent's elution strength is continuously increased as a function of time.

A separation system according to embodiments of the present invention comprises a solvent supply system as described above, the solvent supply system being adapted for supplying a composite solvent, and a separation device adapted for separating compounds of a fluid sample, with the outlet of the solvent supply system being connected to the inlet of the separation device. By utilizing a solvent supply system that is capable of providing a highly precise solvent gradient, the accuracy of the acquired data is considerably improved. In a preferred embodiment, the separation device is a separation column filled with packing material.

In a preferred embodiment, the separation flow path comprises a sample injection unit that is preferably located downstream of the solvent supply system and upstream of the separation device.

In a further preferred embodiment, the separation system is one of: a liquid chromatography system, an electrophoresis system, an electrochromatography system.

Embodiments of the invention can be partly or entirely embodied or supported by one or more suitable software programs, which can be stored on or otherwise provided by any kind of data carrier, and which might be executed in or by any suitable data processing unit. Software programs or routines are preferably applied for determining the required correction of a piston's displacement, and for generating control signals for controlling the piston movement.

BRIEF DESCRIPTION OF DRAWINGS

Other objects and many of the attendant advantages of embodiments of the present invention will be readily appreciated and become better understood by reference to the following more detailed description of embodiments in connection with the accompanied drawing(s). Features that are substantially or functionally equal or similar will be referred to by the same reference sign(s).

FIG. 3 shows a dual piston pump comprising two metering pumps connected in series;

FIG. 10 shows the respective displacement speeds of piston A and piston B as a function of time, whereby the piston movement is corrected by means of a correction pulse.

In FIG. 1, a high pressure solvent delivery system is shown. The solvent delivery system comprises a first solvent delivery line 1 with a first metering pump 2. The first solvent delivery line 1 is adapted for supplying a first solvent A to a mixing tee 3, with the flow rate of solvent A being determined by the movement of the metering pump's piston 4. Furthermore, a second solvent delivery line 5 with a second metering pump 6 is connected to the mixing tee 3. The second solvent delivery line 5 is adapted for supplying a second solvent B to the mixing tee 3, with the rate of solvent B being determined by the movement of piston 7.

Figure 1:
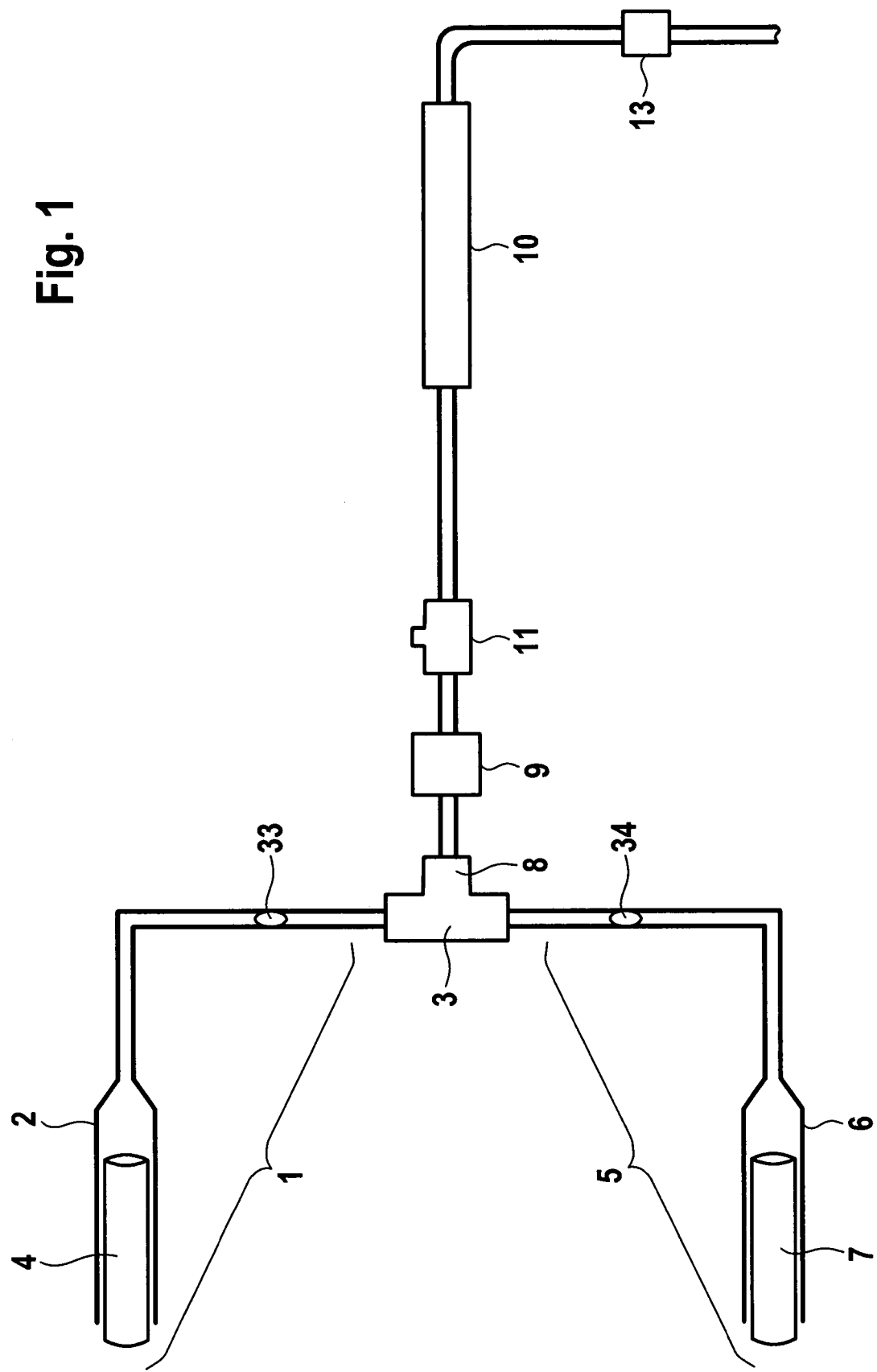
FIG. 1 shows a solvent delivery system comprising a solvent delivery line for solvent A and a solvent delivery line for solvent B.

In the mixing tee 3, the respective volumes of solvent A and solvent B provided by the two solvent delivery lines 1,5 are mixed and at the mixing tee's outlet 8, a composite solvent with a certain percentage of solvent A and a certain percentage of solvent B is provided. A pressure determination unit 9 is located downstream of the mixing tee's outlet 8. The pressure determination unit 9 might e.g. comprise a wire strain gauge or a piezoelectric pressure gauge for determining the composite solvent's pressure.

The high pressure solvent delivery system can be used in the field of liquid chromatography, for supplying a solvent gradient to a high pressure liquid chromatography (HPLC) column. However, the solvent delivery system shown in FIG. 1 might as well be used in any other application where a time dependant composition of two or more solvents is needed. In the embodiment shown in FIG. 1, the outlet 8 of the mixing tee 3 is in fluid communication with a liquid chromatography column 10. The flow path further comprises an injector unit 11 located upstream of the separation column 10. The injector unit 11 permits introducing a volume of fluid sample, a so-called "plug", into the separation flow path. When starting sample analysis, the elution strength of the composite solvent is rather low, and as a consequence, most of the sample components are trapped at the separation column's head. Next, a solvent gradient is applied. In FIG. 2, the solvent gradient is depicted as a function of time. Initially, the composite solvent consists entirely of solvent A, which might e.g. be water. During the time interval 12, the percentage of solvent B is continuously augmented. In general, solvent B often is an organic solvent, like e.g. ethanol or acetonitrile. Because of the increasing amount of organic solvent, the elution strength continually increases during the time interval 12, and the various different moieties of the injected sample are consecutively washed to the separation column's outlet, which is connected to a detection unit 13. The detection unit 13 might e.g. be implemented as an optical absorbance detection unit adapted for monitoring absorbance intensity of the fluid. Whenever a band of a certain sample component passes the detection cell, there will be a corresponding peak in the detector's output signal. Peaks may be characterized with respect to their retention time, which is the time at which the center of the band transits the detector, relative to the time of injection. By integrating the area below a peak, the absorption due to a certain sample component is obtained. If the flow rate through the detection unit is kept constant, the obtained peak area will be directly proportional to the concentration of the corresponding sample component. Accordingly, it has always been tried to keep the flow rate in the separation flow path as constant as possible.

Figure 2:
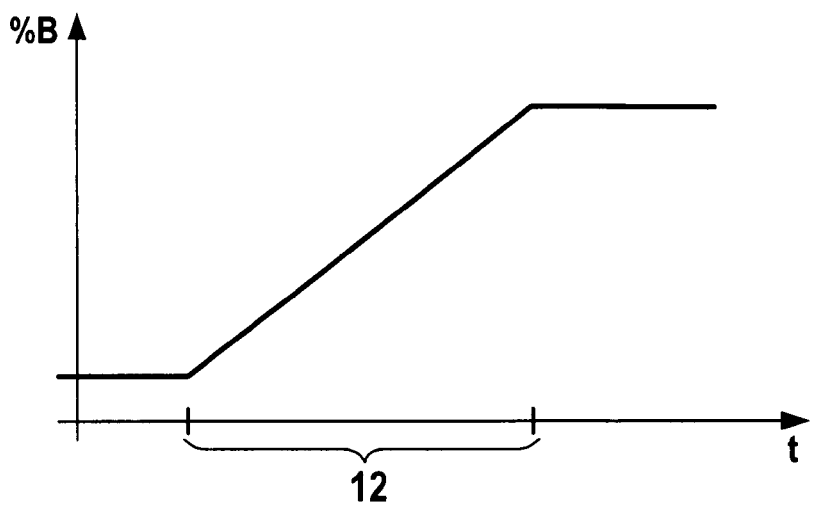
FIG. 2 shows a solvent gradient, whereby the amount of solvent B is linearly increased as a function of time.

In the solvent supply system of FIG. 1, each of the solvent delivery lines 1, 5 comprises one high pressure pump. However, in order to provide for a constant flow of solvent, an arrangement of two pump heads as shown in FIG. 3 can be used instead of a single metering device. The arrangement shown in FIG. 3 comprises a first pump head 14 and a second pump head 15 that is connected in series with the first pump head 14. The first pump's inlet 16 is equipped with a first check valve 17, and the outlet 19 is equipped with a second check valve 20. The outlet 19 is in fluid communication with the inlet 21 of the second pump. During a first phase of operation, the first pump's piston 22 is moved upwards, whereas the second pump's piston 23 performs a downward stroke. Check valve 17 is opened, check valve 20 is closed, and solvent is aspirated. Due to the downward movement of the second pump's piston 23, a flow of solvent appears at the second pump's outlet 24. During a subsequent second phase of operation, piston 22 is moved downwards, whereas piston 23 performs an upward stroke. Piston 22 displaces about twice the volume of piston 23. For this reason, the upward stroke of piston 23 is overcompensated by the downward stroke of piston 22, and there is a resulting flow of solvent at the outlet 24.

A solvent delivery system suited for high pressure liquid chromatography (HPLC) has to supply a composite solvent at a pressure of more than 100 bar. Whenever the pistons 22, 23 change their direction of movement, there will be a discontinuity 25 of system pressure. In order to dampen discontinuities of this kind, the solvent delivery line further comprises a pulse dampener 26. In the pulse dampener 26, the solvent pressure acts against a membrane 27 that separates the solvent conduit from a fluid reservoir 28. This leads to a significant decrease (29) of the pressure discontinuity.

Figure 4:
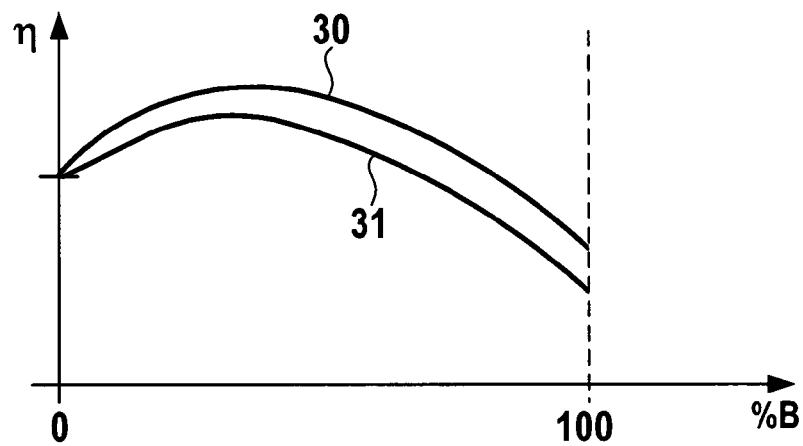
FIG. 4 shows a composite solvent's viscosity as a function of the composite solvent's mixing ratio.

In FIG. 4, the viscosity of the composite solvent is shown as a function of solvent composition, i.e. of the percentage of solvent B. Curve 30 relates to a mixture of water and methanol (MeOH). Curve 31 relates to a mixture of water and acetonitrile (ACN). For both cases, the viscosity of the composite solvent strongly depends on solvent composition. For small amounts of solvent B, the viscosity is rather low, then it rises, and then it drops again as the percentage of solvent B gets large.

The solvent pressure required for establishing predefined solvent flow through the separation column 10 depends on the viscosity of the composite solvent. In fact, the solvent pressure p at the column's head can be written as:

$$p = \text{flow rate} \times \text{hydraulic flow resistance} = \text{flow rate} \times \text{geometry factor} \times \text{viscosity}$$

Hence, the pressure required for conveying the composite solvent through the separation column is directly proportional to the composite solvent's viscosity.

Figure 5:
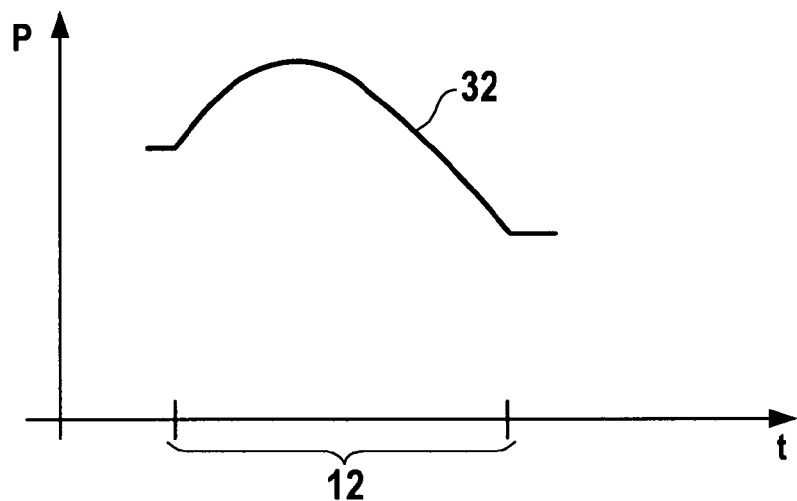
FIG. 5 depicts the time dependence of the composite solvent's pressure when applying a solvent gradient to a separation device.

When supplying a solvent gradient to the separation column 10, the composite solvent's viscosity profile induces a corresponding profile of the solvent pressure measured upstream of the column's inlet. FIG. 5 shows a curve 32 indicating the solvent pressure measured by the pressure determination unit 9 as a function of time when a solvent gradient like the one shown in FIG. 2 is applied. In case of pure water, a pressure of about 270 bar is required for forcing the mobile phase through the stationary phase support of the separation column. With increasing amount of organic solvent, the viscosity of the composite solvent is increased, and accordingly the pressure necessary to maintain the required volumetric flow rate rises up to about 350 bar. When further increasing the amount of organic solvent, the viscosity decreases, and accordingly, the required pressure goes down to about 150 bar.

One of the findings according to embodiments of the present invention is that the solvent pressure's dependence on solvent composition may cause compositional disturbances. In the following, the reason for these disturbances will be explained in more detail. If the pressure detected at the pressure determination unit 9 of FIG. 1 is increased, both the volume of solvent A in the solvent delivery line 1 and the volume of solvent B in the solvent delivery line 5 will be further compressed. In FIG. 1, the volume compression 33 of solvent A and the volume compression 34 of solvent B have been indicated schematically. In the opposite case, if the pressure of the composite solvent drops, both the volume of solvent A in the first solvent delivery line 1 and the volume of solvent B in the solvent delivery line 5 will be subjected to an expansion. The additional impact of solvent compression and solvent expansion in the solvent delivery lines 1,5 implies that the respective piston movements of the metering pumps 2,6 do not solely determine the solvent flow that arrives at the mixing unit 3. In fact, in addition to the piston movements, changes of solvent pressure and corresponding variations of the solvent volumes contained in the solvent delivery lines have to be taken into account.

Figure 6A:
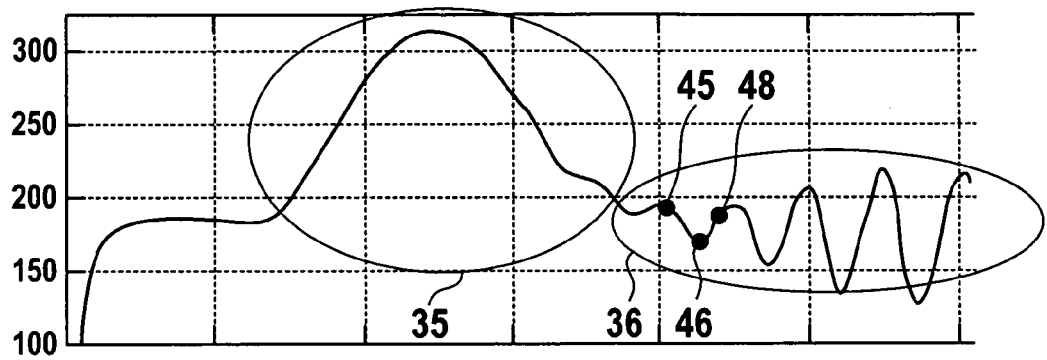
FIG. 6 shows the time dependence of solvent pressure, column flow, solvent composition and piston displacement for the case of a non-corrected piston movement.
Figure 6B:
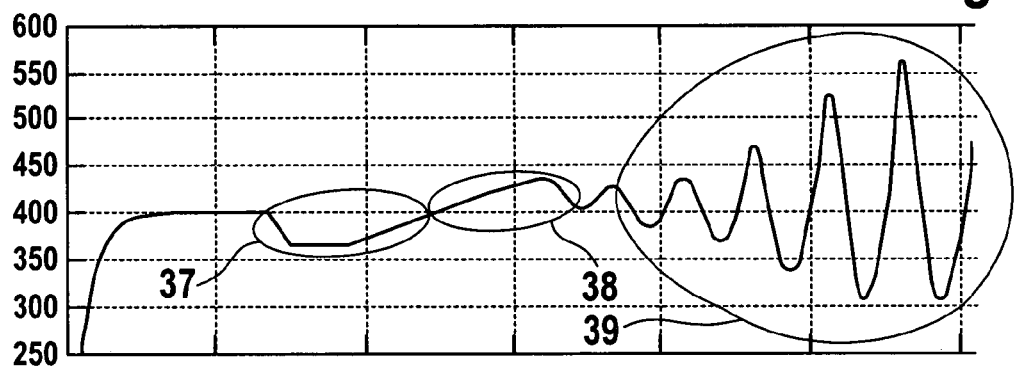

In order to more closely understand the effects due to pressure variations, FIGS. 6A to 6D show a simulated behaviour of several different system parameters when applying a high pressure solvent gradient of $H_2O$ and MeOH to a separation column. In order to enhance the effects to become better visible a compressible liquid flow path A is assumed, e.g. with more damping being installed in flow path A. In FIG. 6A, the pressure of the composite solvent is depicted as a function of time. In region 35, the pressure's behaviour agrees pretty well with the pressure profile shown in FIG. 5. However, in region 36, the pressure of the composite solvent starts to oscillate. A similar behaviour is encountered when monitoring the solvent flow through the separation column as a function of time, which is depicted in FIG. 6B. In region 37, the flow through the column decreases, and in region 38, the flow of the composite solvent increases as a function of time. In region 39, oscillations of the column flow are observed.

Figure 6C:
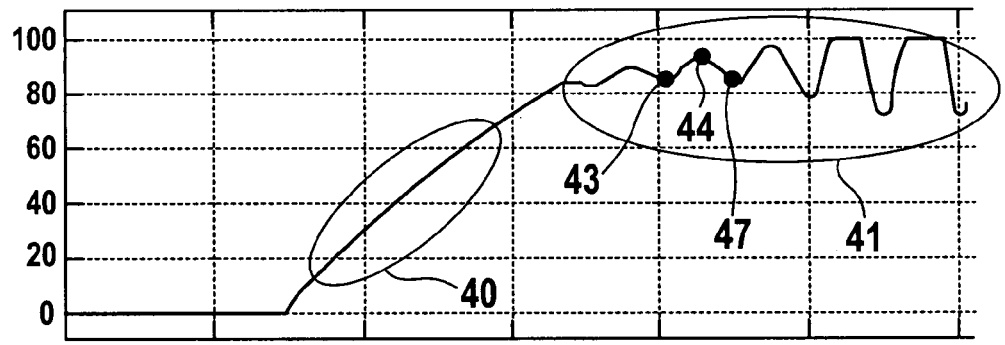

The oscillating behaviour can be understood in view of FIG. 6C, which shows the delivered percentage of solvent B as a function of time. In region 40, the percentage of solvent B increases almost linearly as a function of time. Then, in region 41, oscillations of the composite solvent's composition are observed.

Figure 6D:
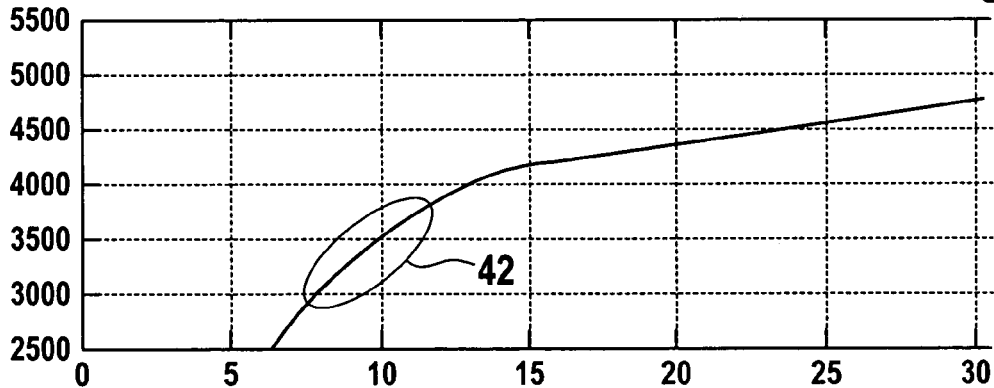

In FIG. 6D, the corresponding piston position is depicted as a function of time. Initially, in region 42, the slope of the piston's position curve is quite large, which corresponds to a large flow rate of solvent A. For generating a solvent gradient, it is necessary to continuously decrease the flow rate of solvent A while linearly increasing the flow rate of solvent B. In order to provide for a linear decrease of the flow rate of solvent A, the slope of the piston's position is continuously reduced.

In the following, the mechanism of the oscillating behaviour depicted in FIGS. 6A, 6B, 6C will be discussed. Let us consider an increase of the amount of solvent B from 85% (cf. reference sign 43 of FIG. 6C) to 95% (cf. reference sign 44 of FIG. 6C). As soon as the modified solvent composition has propagated to the separation column's head, solvent pressure will change in accordance with the modified composition's viscosity. Accordingly, a corresponding decrease of the composite solvent's pressure is observed in the time interval between reference sign 45 and reference sign 46 of FIG. 6A. Now, both the volume of solvent A in solvent delivery line 1 and the volume of solvent B in solvent delivery line 5 expand in accordance with this pressure drop. In dependence on the respective compressibilities $\kappa_A$ of solvent A and $\kappa_B$ of solvent B, additional volumes of solvent A and solvent B are set free. These additional volumes affect the composition of the composite solvent: The relative increase of the flow rate of solvent A will be more significant than the relative increase of the flow rate of solvent B, because in region 41, the absolute flow rate of solvent A is much smaller than the flow rate of solvent B. As a result, the percentage of solvent B might e.g. decrease from 95% to about 87% (cf. reference sign 47 of FIG. 6C). When the modified composition of the solvent mixture reaches the separation column, a corresponding increase of the composite solvent's pressure is observed (cf. reference sign 48 of FIG. 6A).

In the next iteration, this increase of solvent pressure will lead to a corresponding compression of the volumes of solvent A and solvent B in the solvent delivery lines, which will give rise to a modified solvent composition, etc.

From the above discussion, it is clear that the oscillating behaviour is due to an interplay between solvent composition and solvent pressure, with the period of these oscillations being determined by the composite solvent's propagation delay when travelling from the mixing unit to the separation column.

According to embodiments of the present invention, the piston movement A is modified in a way that also the oscillatory behaviour shown in FIGS. 6A, 6B, 6C is avoided. In particular, it is suggested to compensate for a compression or expansion of the solvent volumes contained in the solvent delivery lines, which is due to a variation of solvent pressure, by superposing corresponding corrective displacements on the pistons' movements.

Figure 7A:
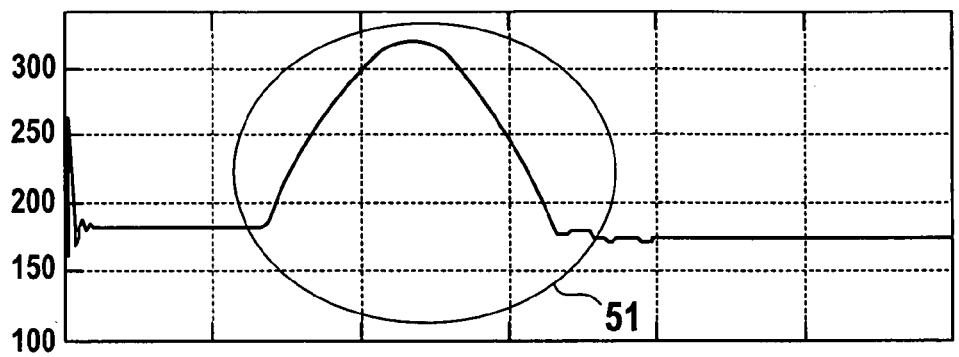
FIG. 7 shows the time dependence of solvent pressure, column flow, solvent composition and piston displacement for the case of a corrected piston movement.
Figure 7B:
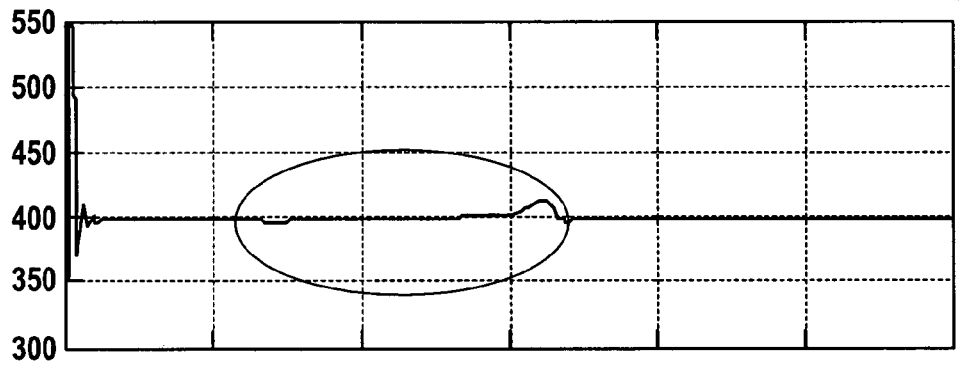
Figure 7C:
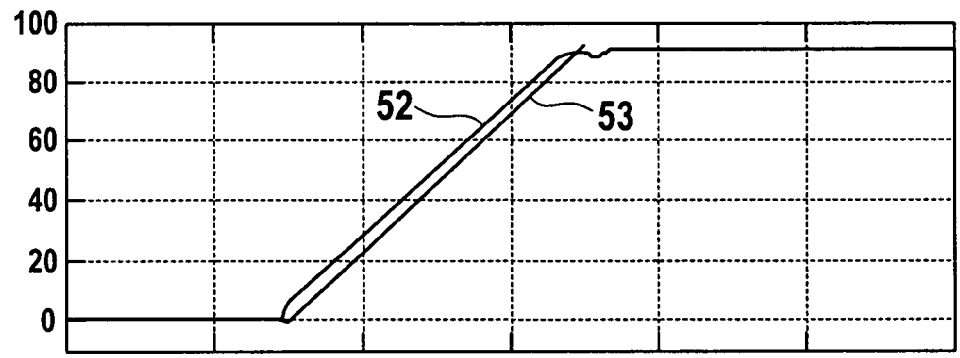
Figure 7D:
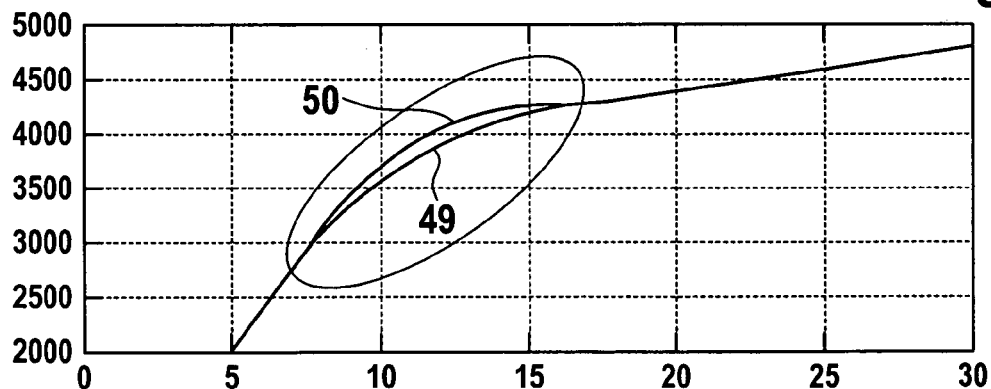

FIG. 7D shows piston position of piston A versus time. From FIG. 7D, it can be seen how the piston movement of piston A is modified. Curve 49 shows the piston movement according to solutions of the prior art, whereas in curve 50, the effects due to pressure variations are taken into account.

When the pressure increases and the solvent volume in the supply flow path is compressed, a corrective movement in the forward direction is superposed on the piston movement, in order to compensate for this compression. When there is a decrease of the composite solvent's pressure, the solvent volume in the supply flow path will expand, and in order to compensate for this expansion, a backward displacement is superposed on the piston movement. Thus, additional solvent quantities pushed into or drawn out of the supply flow paths are compensated for.

The three diagrams in FIGS. 7A, 7B, 7C relate to a pressure-corrected piston movement according to curve 50 of FIG. 7D. FIG. 7A depicts system pressure as a function of time when applying a solvent gradient to the separation column. The corrected piston movement does not influence the viscosity profile of the composite solvent, and therefore, in region 51, the pressure curve still corresponds to the pressure curve shown in FIG. 5. However, due to the corrected piston movement, pressure oscillations (cf. region 36 of FIG. 6A) are suppressed.

FIG. 7B shows column flow of the separation column as a function of time. When comparing the column flow of FIG. 7B with the column flow shown in FIG. 6B, it is obvious that the modified piston movement helps to flatten out flow disturbances. Oscillations of column flow, which have been present in region 39 of FIG. 6B, are entirely suppressed.

FIG. 7C depicts the percentage of solvent B as a function of time. Curve 52 is close to a straight line 53, and accordingly, the amount of solvent B increases linearly as a function of time. In contrast to FIG. 6C, no oscillations of the amount of solvent B are observed. After having reached the maximum, the percentage of solvent B remains constant.

Figure 8A:
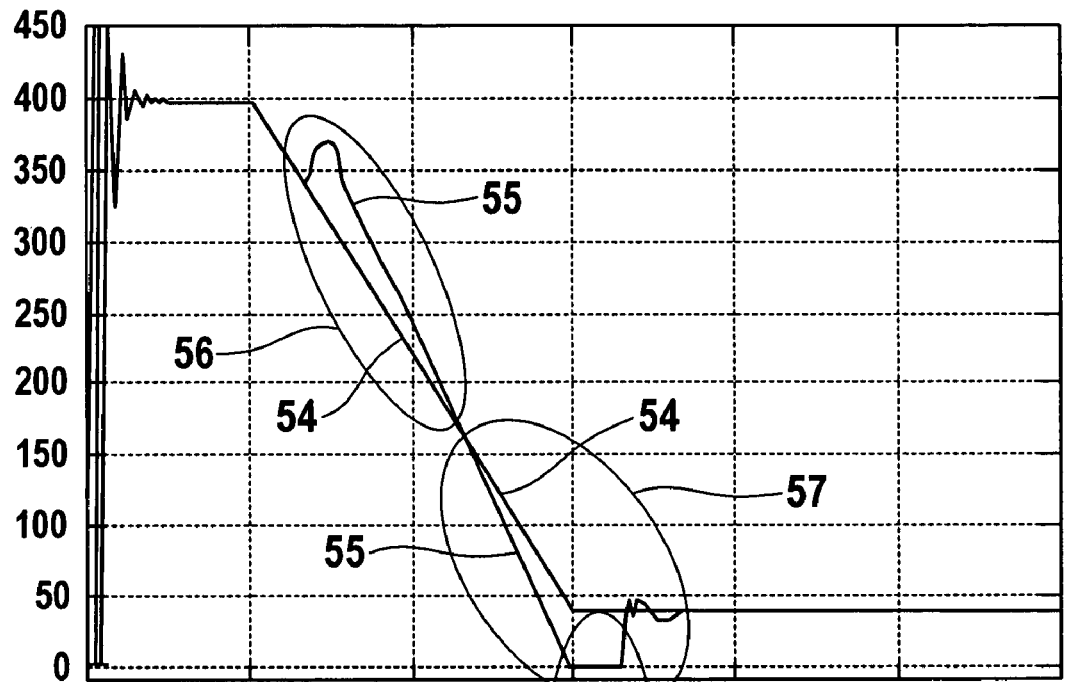
FIG. 8 shows the respective displacement speeds of piston A and piston B as a function of time for the case of a corrected piston movement.

FIG. 8A shows the speed of piston A as a function of time. Curve 54 corresponds to the case that no correction is applied, whereas in curve 55, a corrective movement is superposed on the piston's regular movement. In region 56, the pressure rises as a function of time (cf. FIG. 7A), and the volume of solvent A in the solvent supply flow path is compressed. In order to compensate for this compression of solvent A, a correction in the forward direction is superposed on the piston movement. In region 56, the corrected curve 55 lies above the non-corrected curve 54. After system pressure has reached its maximum, the pressure starts to decrease as a function of time. Region 57 of FIG. 8A is related to this decrease of pressure. The respective volumes of solvent A and solvent B contained in the supply flow paths expand. In order to compensate for this expansion, a correction in the backward direction is superposed on the piston movement. Accordingly, in region 57, the corrected curve 55 lies below the non-corrected curve 54.

Figure 8B:
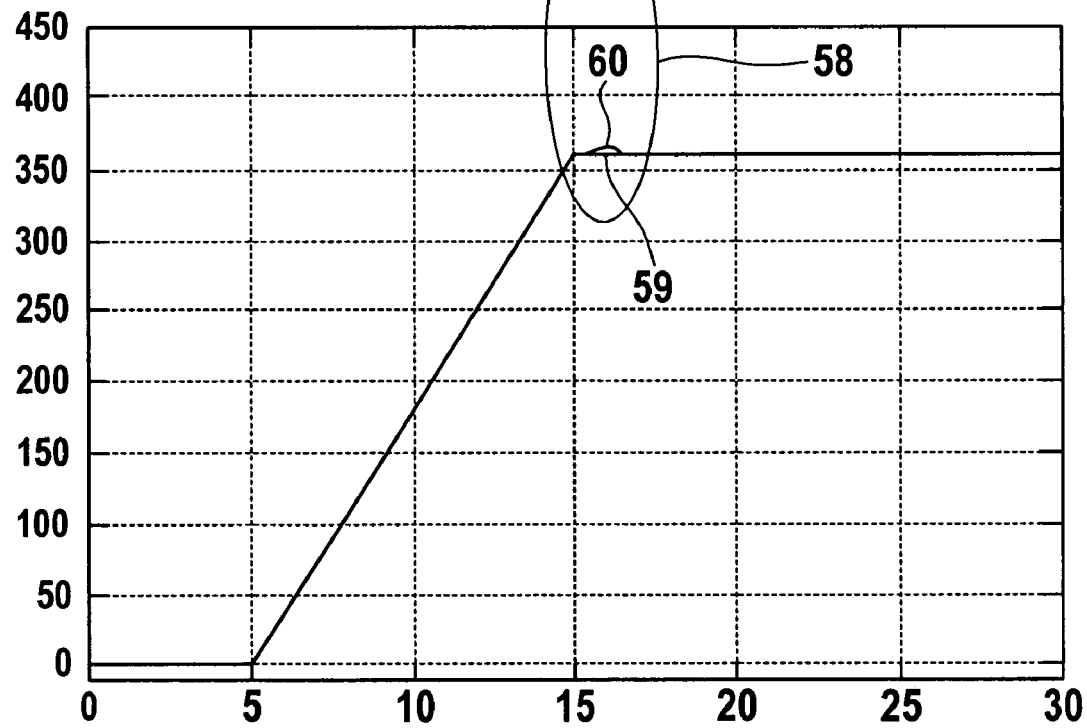

In FIG. 8B, the speed of piston B is depicted as a function of time. The time scale of FIG. 8B coincides with the time scale of FIG. 8A. Comparing FIG. 8A and FIG. 8B, it can be seen that most of the flow correction is performed by modifying the speed of piston A. However, if the corrected speed of piston A drops below zero, which is the case in region 58, it will become necessary to additionally modify the speed of piston B. Accordingly, in region 58, the corrected curve 60 indicating the modified speed of piston B deviates from the non-corrected curve 59. Region 58 is the only region in FIG. 8B where the speed of piston B is modified. This is true only for the case that the flow path for solvent A is substantially weaker than the flow path for solvent B, which is true for the assumed damping installed in the flow path for solvent A.

Figure 9A:
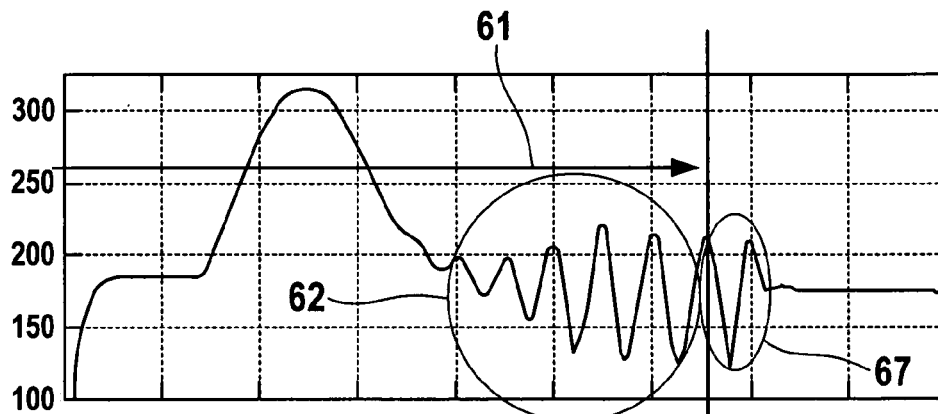
FIG. 9 shows solvent pressure, column flow, solvent composition and piston displacement as a function of time, whereby the piston movement is corrected by means of a correction pulse.
Figure 9B:
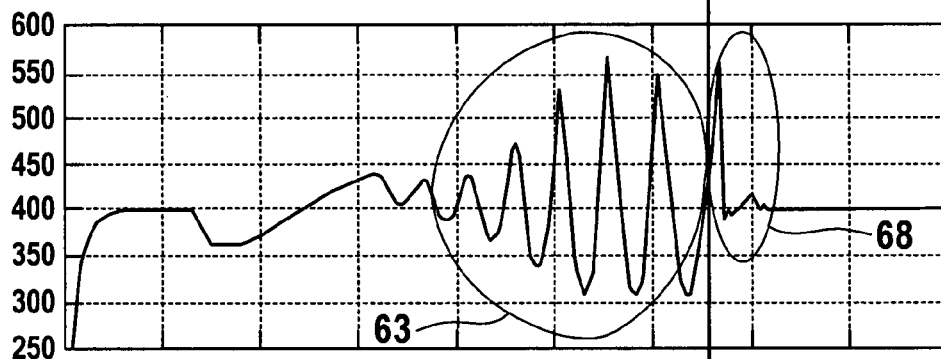
Figure 9C:
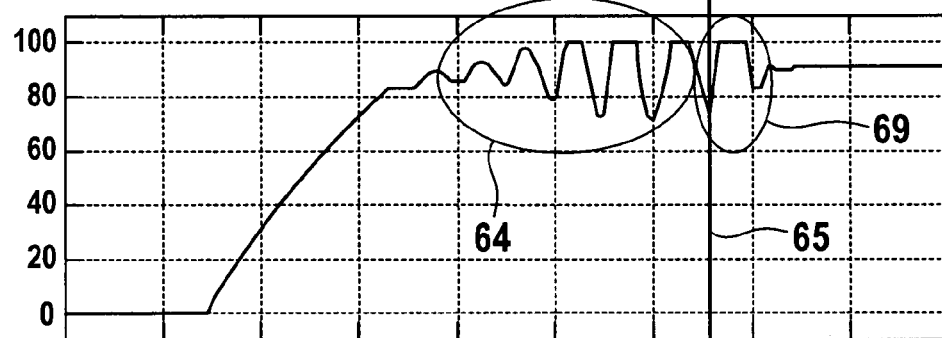
Figure 9D:
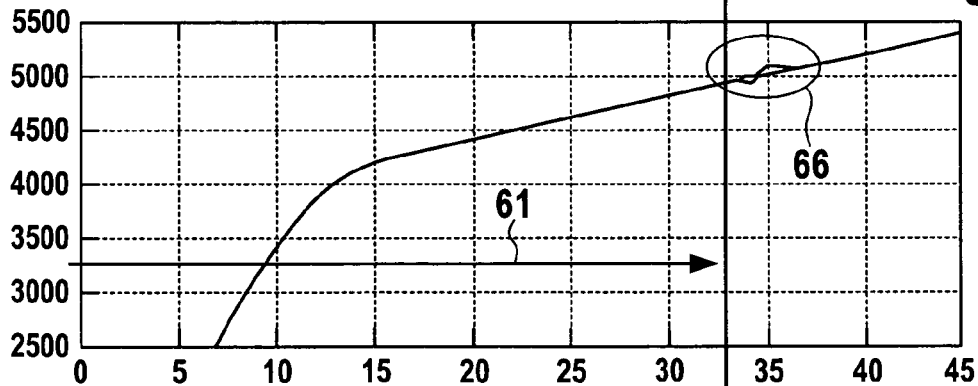

FIGS. 9A to 9D relate to an alternative embodiment of the invention. FIG. 9A shows system pressure as a function of time, FIG. 9B depicts the time dependence of column flow, and in FIG. 9C, the percentage of solvent B is sketched as a function of time. In time interval 61, the solvent delivery system is run uncorrected. Accordingly, in regions 62, 63, 64, stable oscillations occur. In these regions, the system behaviour corresponds to the behaviour shown in FIGS. 6A, 6B, 6C. Then, at a point of time 65, the correction algorithm is activated, and a corrective displacement is superposed on the piston movement. This can be seen in FIG. 9D, which shows the piston position of the metering device for solvent A as a function of time. In time interval 61, the non-corrected piston movement coincides with the piston movement of FIG. 6D. Starting at the point of time 65, a corrective displacement is superposed on the piston movement. The small wave in region 66 of FIG. 9D indicates this correction. In response to this corrective movement, the oscillatory behaviour is dampened in regions 67, 68,69, and stability is achieved almost instantaneously.

FIGS. 10A and 10B relate to the embodiment of FIGS. 9A to 9D and indicate the respective speed of piston A and piston B as a function of time. FIG. 10A relates to the speed of piston A. During time interval 70, the speed of piston A is not subjected to any corrections. Then, at a point of time 71, there is a steep change 72 counteracting the oscillatory behaviour. FIG. 10B relates to the speed of piston B. In time interval 70, the speed of piston B is not modified at all. After flow correction is started at the point of time 71, most of the correction is performed by the metering device of the solvent delivery line for solvent A. However, whenever the speed of piston A drops below zero, it will be necessary to modify the speed of piston B. For example, in region 73, there exist corrections 74, 75 superposed on the speed of piston B that correspond to time intervals where the speed of piston A is below zero. The flow corrections shown in FIGS. 10A and 10B enforce a stabilization of solvent composition and column flow.

The invention claimed is:

1. A solvent supply system comprising:
a supply flow path;
a first metering device with a piston, the first metering device being configured for supplying a first solvent to a mixing unit;
a second metering device with a piston, the second metering device being configured for supplying a second solvent to the mixing unit;
the mixing unit being configured for mixing the first and the second solvent and for supplying a composite solvent with a mixing ratio of the first and the second solvent into the supply flow path; and
a control unit configured for controlling the piston movements of the first and the second metering device to reduce disturbances of the composite solvent's mixing ratio caused by pressure variations in the supply flow path such that the mixing ratio becomes substantially independent of a variation of the solvent pressure of the composite solvent in the supply flow path; wherein
the control unit is adapted for compensating for an increase of the solvent pressure by superposing a corresponding forward displacement on the movement of the pistons, and for compensating for a decrease of the solvent pressure by superposing a corresponding backward displacement on the movement of the pistons.

2. The supply flow path of claim 1, further comprising at least one of the features:
a pressure determination unit adapted for determining the solvent pressure at the supply flow path's outlet;
the control unit is adapted for such controlling the movement of the piston that a flow rate at the supply flow path's outlet is stabilized;
the control unit is adapted for compensating for an additional compression of expansion flow due to the variation of the solvent pressure by modifying the metering devices's piston movement in a way that the additional solvent quantity pushed into or drawn out of the supply flow path is compensated for; and
a forward displacement of the piston corresponds to a volume compression of the solvent in the supply flow path, and wherein a backward displacement of the piston corresponds to a volume expansion of the solvent in the supply flow path.

3. The solvent supply system according to claim 1, wherein the first supply flow path is adapted for supplying a first solvent to a mixing unit, the solvent supply system further comprising:
a second supply flow path comprising a second metering device with a piston, the second supply flow path being adapted for supplying a second solvent to the mixing unit,
the mixing unit being adapted for mixing the first and the second solvent and for supplying a composite solvent with a mixing ratio of the first and the second solvent,
with the control unit being adapted for such controlling the piston movements of the first and the second metering device that the mixing ratio becomes substantially independent of a variation of the solvent pressure of the composite solvent.

4. The solvent supply system of claim 3, comprising at least one of the features:
- the control unit is adapted for compensating for an additional compression or expansion flow due to the variation of the solvent pressure by such modifying the metering devices' piston movements, in each of the first and the second supply flow path, that solvent quantities pushed into or drawn out of the respective supply flow paths are compensated for;
- the control unit is adapted for counteracting an expansion or compression of the solvent volumes in the supply flow paths, which is due to a variation of the solvent pressure, by compensatory movements superposed on the piston movements;
- the control unit is adapted for compensating for an increase of the solvent pressure by superposing corresponding forward displacements on the piston movements, and for compensating for a decrease of the solvent pressure by superposing corresponding backward displacements on the piston movements;
- the control unit is adapted for antagonizing oscillations of the composite solvent's mixing ratio due to variations of the composite solvent's pressure by superposing a compensatory stimulus pulse on at least one of the first and the second metering device's piston movement;
- the control unit is adapted for such controlling the piston movements of the first and the second metering device that the composite solvent is provided at a constant flow rate;
- the control unit is adapted for continuously varying the ratio of the first and the second solvent as a function of time;
- the control unit is adapted for varying the ratio of the first and the second solvent in the composite solvent according to a gradient;
- the control unit is adapted for deriving the solvent pressure of the composite solvent from the ratio of the first and the second solvent, which determines the composite solvent's viscosity.

5. The solvent supply system of claim 3, wherein the control unit is adapted for deriving the additional expansion or compression flow from one or more of the following parameters:
- actual pressure of at least one of: the first solvent, the second solvent, the composite solvent;
- system elasticity of supply flow path components;
- respective compressibilities in the first and the second supply flow path;
- actual piston positions of the metering devices, which determine the respective solvent volumes contained in the first and the second supply flow path.

6. The solvent supply system of claim 3, comprising at least one of the features:
- the mixing unit is a mixing tee;
- forward displacements of the pistons correspond to volume compressions of the first and the second solvent in the first and the second supply flow path, and wherein backward displacements of the pistons correspond to volume expansions of the first and the second solvent in the first and the second supply flow path;
- a pressure determination unit located downstream of the mixing unit's outlet, the pressure determination unit being adapted for determining the pressure of the composite solvent;
- the mixing ratio is a time-dependent mixing ratio;
- for each of the first and the second supply flow path, a respective first and second compressibility is determined;
- the variation of the solvent pressure corresponds to a variation of the composite solvent's viscosity;
- at least one of the first and the second supply flow path further comprises a damping unit;
- the solvent supply system is implemented as a part of a microfluidic device;
- the mixing unit's outlet is connected to a separation device, with the composite solvent being used as a mobile phase for separating compounds of a fluid sample;
- the first solvent is water, and wherein the second solvent is either one of ethanol and acetonitrile.

7. The solvent supply system of claim 3 being adapted for supplying a composite solvent, further comprising
- a separation device adapted for separating compounds of a fluid sample, with the outlet of the solvent supply system being connected with the separation device's inlet.

8. The solvent supply system of claim 7, comprising at least one of the features:
- a sample injection unit located downstream of the solvent supply system, the sample injection unit being adapted for introducing a fluid sample to the separation system;
- the composite solvent is used as a mobile phase for separating compounds of a fluid sample;
- the separation system is one of: a liquid chromatography system, an electrophoresis system, an electrochromatography system.

9. A method for generating a composite solvent with a time-dependent solvent composition, the method comprising:
- providing a first solvent using a first metering device that is part of a first supply flow path;
- providing a second solvent using a second metering device that is part of a second supply flow path;
- mixing the first and the second solvent and generating a composite solvent with a time-dependent mixing ratio of the first and the second solvent;
- monitoring the solvent pressure of the composite solvent;
- controlling piston movements of the first and the second metering device to reduce disturbances of the mixing ratio of the composite solvent caused by pressure variations of the composite solvent in a way that the mixing ratio becomes substantially independent of the solvent pressure of the composite solvent, comprising compensating for an expansion or compression of the first solvent in the first supply flow path that is due to the pressure variation by superposing a corresponding corrective forward or backward displacement on the first metering device's piston movement, and compensating for an expansion or compression of the second solvent in the second supply flow path that is due to the pressure variation by superposing a corresponding corrective forward or backward displacement on the second metering device's piston movement.

10. The method of claim 9, further comprising:
- counteracting an expansion or compression of the solvent volume in the supply flow path, which is due to the variation of the solvent pressure, by superposing a compensatory movement on the piston movement.

11. The method of claim 9, further comprising at least one of the features:
- counteracting an expansion or compression of the solvent volumes in the first and the second supply flow path, which are due to the variation of solvent pressure, by superposing compensatory movements on the piston movements; and antagonizing oscillations of the composite solvent's mixing ratio due to variations of the composite solvent's pressure by superposing a compensatory stimulus pulse on at least one of the first and the second metering device's piston movement.

* * * * *